United States Patent [19]

Sharpe et al.

[11] Patent Number: 5,433,722

[45] Date of Patent: Jul. 18, 1995

[54] LIGATURE CARRIER FOR ENDOSCOPIC USE

[75] Inventors: Leslie A. Sharpe, Edina, Minn.; Francis C. Peterson, Prescott, Wis.

[73] Assignee: Sharpe Endosurgical Corporation, St. Paul, Minn.

[21] Appl. No.: 93,451

[22] Filed: Jul. 19, 1993

Related U.S. Application Data

[63] Continuation of Ser. No. 818,180, Jan. 8, 1992, abandoned.

[51] Int. Cl.$^6$ .............................................. A61B 17/00
[52] U.S. Cl. ................................ 606/148; 606/139; 606/144; 606/222; 606/225
[58] Field of Search ............... 606/139, 144, 145, 147, 606/148, 181, 182, 184, 185, 187, 222, 223, 225; 604/192, 194, 196

[56] References Cited

U.S. PATENT DOCUMENTS

| | | | |
|---|---|---|---|
| 43,098 | 6/1864 | Cooper | 606/144 |
| 1,135,465 | 4/1915 | Pollock | 606/182 |
| 1,539,221 | 5/1925 | Tennant | 606/147 |
| 1,640,311 | 8/1927 | Dawes | 606/182 X |
| 1,822,330 | 9/1931 | Ainslie | 606/145 |
| 2,512,882 | 6/1950 | Truesdale | 604/196 |
| 2,738,790 | 3/1956 | Todt, Sr. et al. | 606/145 |
| 3,840,017 | 10/1974 | Violante . | |
| 3,995,619 | 12/1976 | Glatzer | 606/170 |
| 4,164,225 | 8/1979 | Johnson . | |
| 4,194,505 | 3/1980 | Schmitz | 604/196 |
| 4,235,238 | 11/1980 | Ogiu et al. | 606/145 |
| 4,244,370 | 1/1981 | Furlow et al. . | |
| 4,378,019 | 3/1983 | Yamada | 606/187 |
| 4,596,249 | 6/1986 | Freda et al. . | |
| 4,614,187 | 9/1986 | Mulhollan et al. . | |
| 4,841,888 | 6/1989 | Mills et al. . | |
| 4,874,375 | 10/1989 | Ellison | 604/164 |
| 4,935,027 | 6/1990 | Yoon . | |
| 5,047,039 | 10/1991 | Avant et al. | 606/148 |
| 5,149,329 | 9/1992 | Richardson | 128/898 |
| 5,281,237 | 1/1994 | Gimpelson | 606/144 |

FOREIGN PATENT DOCUMENTS

| | | | |
|---|---|---|---|
| 18602 | of 1909 | United Kingdom | 606/139 |
| 433913 | 11/1974 | U.S.S.R. . | |
| 969254 | 10/1982 | U.S.S.R. | 606/144 |

OTHER PUBLICATIONS

WISAP, Minimal Invasive Surgery, Semm System, Instruments.

Primary Examiner—Stephen C. Pellegrino
Assistant Examiner—Jeffrey A. Schmidt
Attorney, Agent, or Firm—Merchant, Gould, Smith, Edell, Welter & Schmidt

[57] ABSTRACT

A surgical instrument having a surgeon operable control handle for advancing a needle to pierce tissue and to carry a ligature through the pierced tissue.

4 Claims, 3 Drawing Sheets

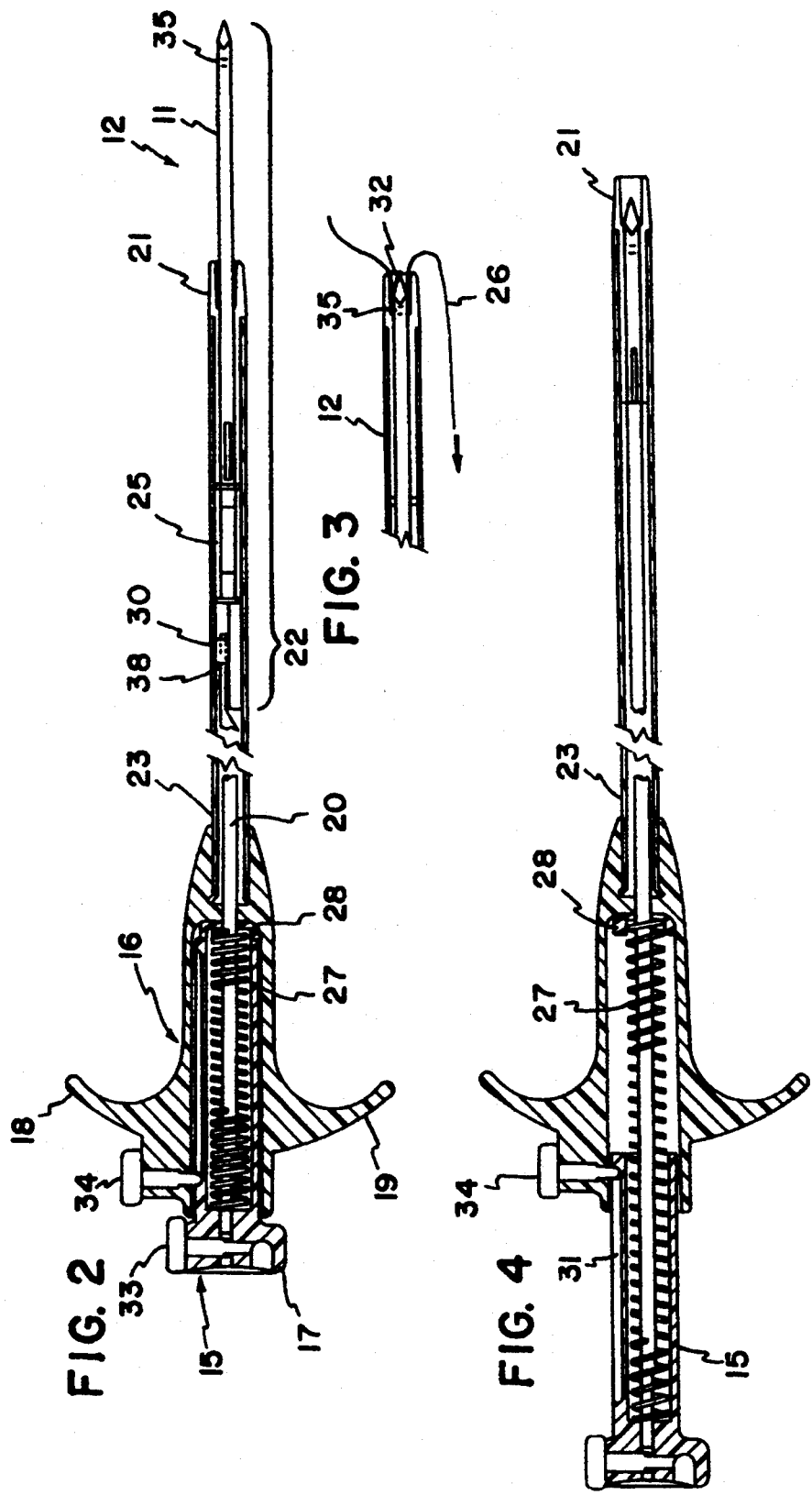

LIGATURE CARRIER FOR ENDOSCOPIC USE

This is a continuation of application Ser. No. 07/818,180, filed Jan. 8, 1992 now abandoned.

BACKGROUND OF THE INVENTION

1. Field of the Invention

The present invention relates to surgical instruments for use during laparoscopic surgery. More particularly, the invention is directed to an endoscopic ligature carrier for use inside the abdominal cavity.

2. Description of the Prior Art

The typical laparoscopic surgical procedure begins with the puncture of the patient's abdominal wall and the placement of an access port. Next, gas is admitted to the abdominal cavity partially inflating it, forming a pneumoperitoneum. A laparoscope or endoscope is next inserted through the access port to permit viewing of the organs during the surgical procedure. Typically the laparoscope has both an eyepiece and a video monitor to permit visualization of the surgical field by the surgeon. Additional access ports may be located elsewhere on the abdominal wall to permit insertion of surgical instruments into the operating field. Access ports come in a variety of diameters and 5, 7 and 11 millimeter ports are widely used for surgery within the peritoneal cavity. Surgical instruments for use through such ports are readily available to surgeons specializing in endoscopic surgery.

Many endoscopic ligation procedures are preformed with instruments such as the SEEM Emergency Needle depicted in FIG. 9. In use, the ligature is threaded through the "eye" of the "needle" and positioned next to the tissue to be ligated. The surgeon pushes the needle through the tissue and the needle carries the ligature through the tissue. The ligature is next grasped from the protruding needle and is removed from the needle. This process passes the ligature through the tissue. This prior art tool has an exposed tip and the ligature is free to slide in the eye of the needle throughout the procedure. These two attributes render the prior art tool difficult to use.

BRIEF SUMMARY OF THE INVENTION

In contrast to the traditional ligature carriers, the present invention provides for positive restraint of the ligature during the procedure and the tip of the needle is only exposed while the tissue is being pierced. Structurally the endoligature carrier has a surgeon operated control handle which can be manipulated to extend a needle from a sheath. The needle tip may be retracted into the blunt nose of the instrument to facilitate placement of the needle against the tissue to be pierced. The blunt nose permits placement without the risk of tissue trauma. While the needle is in the retracted position the ligature is "trapped" by the instrument and will not slide out of engagement with the needle.

BRIEF DESCRIPTION OF THE DRAWING

Throughout the several figures of the drawing like reference numerals are used to identify identical structure, wherein:

FIG. 2 is a crossection of the surgical instrument depicting the needle in the exposed or extended position;

FIG. 3 is a crossection of the operating portion of surgical instrument depicting the needle withdrawn into the sheath and grasping a ligature;

FIG. 4 is a crossection of the surgical instrument depicting the needle in the fully retracted position;

DETAILED DESCRIPTION OF THE EXEMPLARY EMBODIMENT

Figures 1, 9:
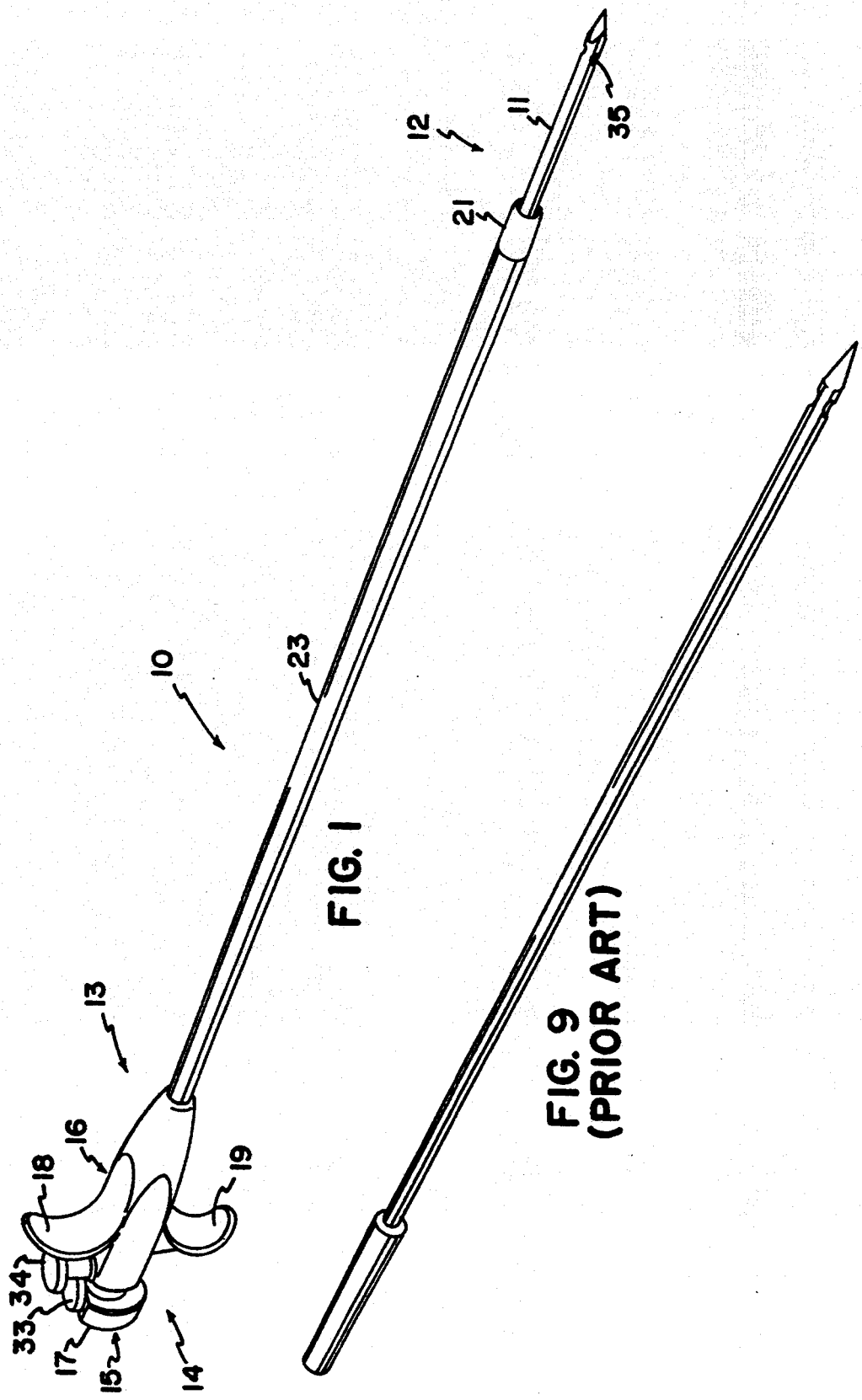
FIG. 1 is a perspective view of the assembled surgical instrument.

FIG. 1 is a perspective view of the endoligature carrier 10. The instrument 10 has an operating portion 12 and a posterior section 13. The posterior section 13 includes the control handle structures generally designated 14. The control handle 14 is grasped by the surgeon and the operating portion 12 is inserted into the body cavity through a suitable access port. In use, the surgeon operates the control handle 14 to manipulate the operating portion 12 of the instrument. The operating portion 12 includes the needle 11 and the blunt nose piece 21.

The control handle 14 includes a rear grip structure 15 and a foregrip structure 16. In use, the rear grip 15 and foregrip 16 are squeezed together to extend the needle 11 from the sheath 23. The preferred rear grip form is a pommel 17, while the preferred foregrip 16 form comprises a pair of complimentary finger loops 18 and 19. These grip structures together form a symmetrical control handle grip. This symmetrical grip arrangement makes the instrument operable with either the left or right hand. The symmetry also permits the instrument to be operated in an upright position or an inverted position. The assembly screws 33 and 34 provide the surgeon with a tactile and visual reference for the orientation of the operating portion 12. The preferred semi-circular finger loops 18 and 19 may receive the forefinger and middle finger of the surgeon while the surgeon's thumb rests on the pommel 17. This preferred control handle 14 also can readily accept the surgeon's middle and ring finger on the loops 18 and 19 and palm on the pommel 17. This ambidextrous multi-position control handle 14 is also compact and light weight which materially aids the surgeon's control of the operating portion of the instrument.

The grip structures are preferably molded of medical grade polysulfone plastic with the posterior section 13 molded onto a stainless steel sheath 23. In general the preferred length of the sheath 23 is approximately 30 cm while the preferred diameter of the sheath 23 is 6.5 mm.

FIG. 2 is a crossection of the instrument depicting the needle 11 in the extended position. The drawing shows the needle assembly 22 which includes a needle carrier 25 which supports the needle 11 within the lumen 37 of the sheath 23. This needle carrier 25 is preferably formed of polysulfone plastic molded onto the stainless steel needle 11 body. The needle carrier 25 has a plug 30 formed on the rear portion to adapted to engage a cooperating slot 38 formed in the connector rod 20. These structures together couple the needle assembly 22 to the connecting rod 20. When the surgeon squeezes the rear grip 15 into the foregrip 16 the tubular bushing portion of the needle carrier 25 bottoms out against the rear section of the blunt nose piece 21, limiting the extension of the needle 11 beyond the end of the instrument. In use the surgeon will squeeze the grip structures together exposing the aperture 35 in the needle assembly 22, which permits threading of a length of ligature 26 into the instrument 10.

FIG. 3 is a fragmentary section of the operating portion 12 and shows a length of ligature 26 loaded into the instrument 10. When the surgeon relaxes his grip, the needle 11 partially retracts into the blunt nose piece 21 which wedges the ligature 26 between the needle aperture 35 and the interior section of the nose piece 21. Since the force exerted by the spring 27 is low in this retracted position the ligature 26 is firmly but gently held in position. It is important to note that the sharp tip 32 of the needle is within the blunt nose piece 21 in this partially retracted or "ligature retaining" position.

FIG. 4 shows the instrument in the fully retracted position. Here the assembly screw 34 bottoms out in channel 31 formed in rear grip 15 to define the location of the needle in the retracted position. The assembly screw 34 in the foregrip 16 also holds the rear grip 15 in the foregrip structure, while assembly screw 33 connects the rear grip 15 to one end of the connector rod 20. With the screws removed the connector rod 20 and attached needle carrier 25 can be removed, from the sheath 23 by movement toward the rear. With the connector rod 20 removed the needle carrier 25 assembly can be detached from the connector rod 20 structure for cleaning. However, in general, the needle carrier 25 will form a disposable assembly which is discarded after a single surgical use. In a similar fashion the nose piece 21 is preferably molded of a polysulfone plastic and is readily removed from the sheath 23 and cleaned or discarded after use. In embodiments where the entire instrument 10 is disposable, the assembly screws may be replaced with pins preventing inadvertent or unauthorized disassembly. Also where the entire instrument is discarded after use it may be preferable to form the disposable needle carrier 25 from a self lubricating plastic material, such as polypropylene.

The foregrip assembly 16 also contains a rubber gas seal 28 which encircles the circular connector rod 20, which prevents passage of fluid or gas through the instrument, and therefore maintains pneumoperitoneum, and sterility of the surgical field. A suitable gas seal may be formed of Kraton thermoplastic rubber.

Several elements cooperate together to improve the "feel" of the instrument. The lumen 37 of the sheath 23 is drawn stainless steel tubing with tightly controlled interior diameter and smoothness. Together the lumen 37 and carrier 25 reduce the friction and stiction associated with needle movement, this permits the use of a relatively low force retraction spring 27 improving the tactile feedback to the surgeon.

Figure 5:
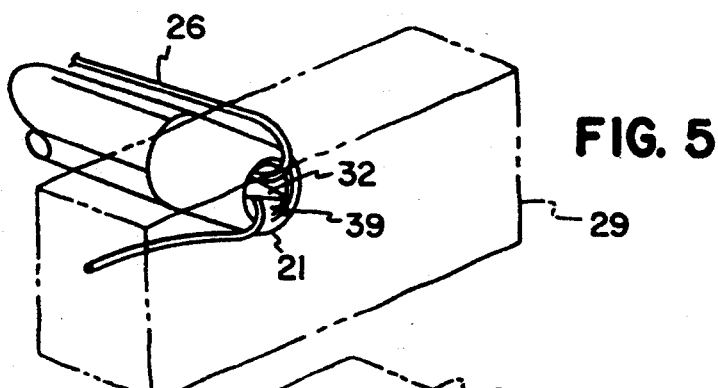
FIG. 5 is a perspective view of the operating portion of the instrument adjacent a mass of tissue.
Figure 6:
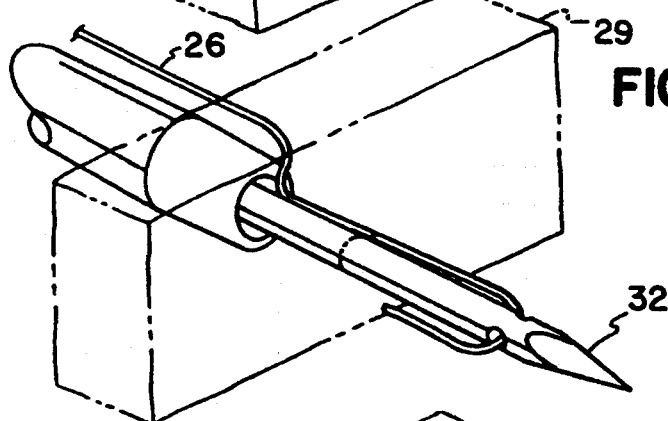
FIG. 6 is a perspective view of the operating portion of the instrument adjacent a mass of tissue with the needle piercing the tissue, and carrying the ligature into position.
Figure 7:
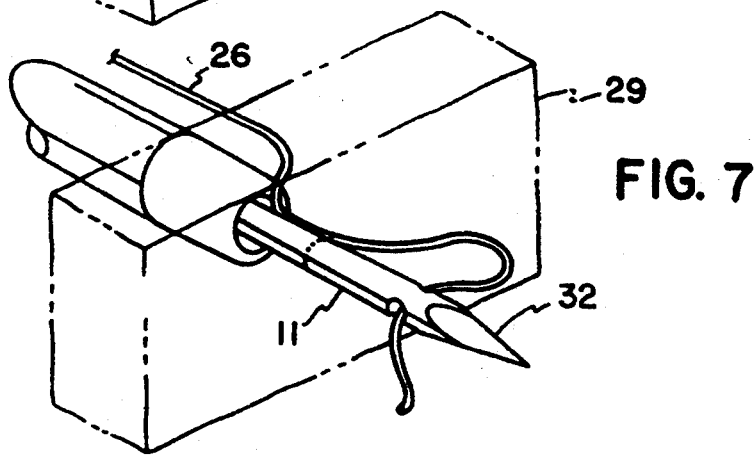
FIG. 7 is a perspective view of the operating portion of the instrument adjacent a mass of tissue with the needle partially retracted forming a loop in the ligature; and, FIG. 8 is a perspective view of the operating portion of the instrument adjacent a mass of tissue with the needle partially retracted and the loop of the ligature removed from the instrument; and, FIG. 9 is a typical prior art needle structure.
Figure 8:
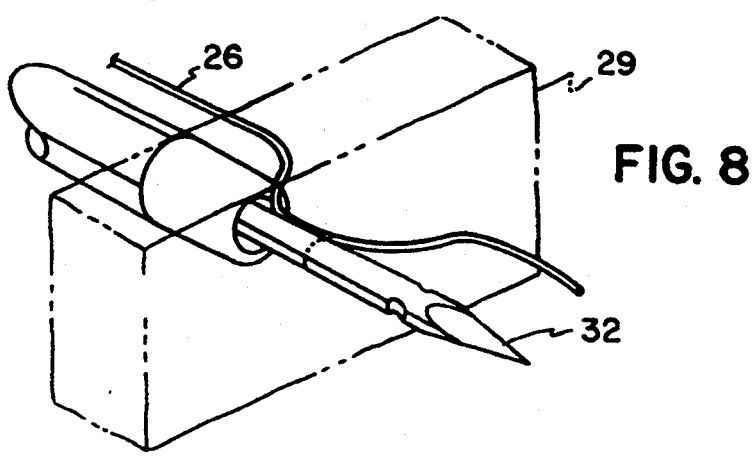

FIG. 5–FIG. 8 show the instrument 10 in use and these drawings should be considered together. In general the surgeon will load a ligature 26 into the instrument 10 and release pressure on the rear grip 15 so that the instrument retains the ligature 26 and the needle tip 32 is withdrawn into the blunt nose piece as seen in FIG. 5. In this position the surgeon can use the blunt nose 21 for blunt dissection to tissues exposing the tissue mass 29 for ligation. As best seen in FIG. 5 the ligature 26 is withdrawn into the blunt nose piece 21. In this fully retracted position the ligature 21 is restrained in a ligature reception area 39 by contact between the ligature 26 and the blunt tip 21. It should be appreciated that the retraction spring 27 is slightly compressed while the ligature is retrained and that the ligature reception area is recessed from the terminal end on the blunt nose piece 21. With the instrument well positioned as shown in figure the surgeon may depress the pommel 17 to force the needle tip 32 through the tissue mass 29 as seen in FIG. 6. This procedure draws the ligature 26 through the tissue mass 29. Slight relaxation of pressure on the grip structures causes the tip 32 to retract slightly forming a loop of ligature near the needle aperture 35. FIG. 7 shows the ligature 26 looped through the aperture in the needle tip 32. It is also possible to form the aperture as a T-shaped slot, with one portion of the aperture extending to the surface of the needle 11, so that the ligature 26 can be placed in the needle without having to thread or un-thread the ligature through a closed shape such as the needle aperture 35 (FIG. 3). For purposes of this disclosure slots which communicate with the surface of the needle 11 should be considered ligature reception apertures. In FIG. 8 another instrument has withdrawn the ligature loop from the instrument. At this point the instrument can be removed from the tissue mass and other tools can be used to capture and control the ligature 26 for a knot tying procedure. This sequence of drawings illustrate several features of the invention. The ability to use the blunt nose 21 of the instrument to place, the needle 11 speeds the ligation procedure while minimizing risk of tissue trauma. Positive retention of the ligature 26 in the instrument during placement eliminates the risk of the ligature 26 from slipping out of the instrument 10. Also the extension of the needle tip 32 beyond the nose piece 21 is limited by the geometry of the instrument and therefore limits the depth that the needle can pierce tissue. In an endoscopic procedure where the depth of visual field is limited, knowledge of this distance permits confidence that tissues beyond the mass 29 will not be injured. Also inadvertent release of the instrument permits the spring 27 to immediately retract the needle tip 32 into the nose piece 21 enhancing patient safety.

What is claimed:

1. A surgical instrument comprising:
    a control handle having a foregrip and a rear grip, said foregrip slidably mounted to said rear grip and thereby adapted to be compressed together;
    an elongate substantially straight sheath coupled to said control handle, said sheath having a lumen, said sheath being terminated with a blunt nose piece having a central bore in communication with said lumen and a terminal end, said bore defining a ligature reception area recessed from the terminal end of said blunt nose piece;
    a control rod located in said lumen and connected to said handle;
    a needle assembly coupled to said control rod, said needle assembly including a needle, said needle having a tip and having reception aperture for a ligature formed in said needle proximate said tip, to accommodate a ligature when it is placed in said reception aperture, such that the ligature passes completely through said reception aperture to a point beyond said needle;

said needle assembly having a needle carrier for locating and supporting said needle for motion along the axis of said lumen;

whereby said needle may be extended out of said bore of said blunt nose piece by operation of said control handle, defining a first extended position;

and whereby said needle may be retracted into said bore of said nose piece by operation of said control handle defining a second retracted position;

a retraction spring located proximate said control handle and in contact with said foregrip and in contact with said rear grip, so that when the ligature abuts within the bore of said nose piece, said retraction spring is slightly compressed, for biasing said needle into said second retracted position;

whereby the ligature in said reception aperture abuts within the bore of said nose piece to retain the ligature in said instrument when said spring biases said needle into said second position.

2. The surgical instrument of claim 1 wherein said sheath is a straight tube.

3. The surgical instrument of claim 1 wherein said needle is straight.

4. The surgical instrument of claim 1 wherein said needle carrier has a diameter which is substantially the same as the interior diameter of said lumen.

* * * * *

UNITED STATES PATENT AND TRADEMARK OFFICE
CERTIFICATE OF CORRECTION

PATENT NO. : 5,433,722
DATED : July 18, 1995
INVENTOR(S) : Leslie A. Sharpe et al It is certified that error appears in the above-indentified patent and that said Letters Patent is hereby corrected as shown below:

In column 1, line 66, please delete "crossection" and insert therefor --cross section--

In column 2, lines 1, 4, and 63, please delete the word "crossection" and insert therefor --cross section--

In column 2, line 40, please delete the word "complimentary" and insert therefor --complementary--

In column 3, line 2, after the word "portion", please delete "to"

In column 3, line 68, after the word "piece", please insert --21--

In column 4, line 12, after the word "in", please insert --the--

Signed and Sealed this

Nineteenth Day of December, 1995

Attest:

BRUCE LEHMAN

Attesting Officer

Commissioner of Patents and Trademarks